US008053466B2

(12) United States Patent
Lelandais

(10) Patent No.: US 8,053,466 B2
(45) Date of Patent: Nov. 8, 2011

(54) OXATHIANE DERIVATIVE AS PERFUMING INGREDIENT

(75) Inventor: Patrick Lelandais, St-Julien-en-Genevois (FR)

(73) Assignee: Firmenich SA, Geneva (CH)

( * ) Notice: Subject to any disclaimer, the term of this patent is extended or adjusted under 35 U.S.C. 154(b) by 509 days.

(21) Appl. No.: 12/305,595

(22) PCT Filed: Jun. 14, 2007

(86) PCT No.: PCT/IB2007/052263
§ 371 (c)(1),
(2), (4) Date: Dec. 18, 2008

(87) PCT Pub. No.: WO2008/004145
PCT Pub. Date: Jan. 10, 2008

(65) Prior Publication Data

US 2009/0285769 A1 Nov. 19, 2009

(30) Foreign Application Priority Data

Jul. 4, 2006 (WO) .................. PCT/IB2006/052235

(51) Int. Cl.
*A61K 31/39* (2006.01)
*C07D 327/06* (2006.01)

(52) U.S. Cl. .......................................... 514/433; 549/14

(58) Field of Classification Search .................. 514/433; 549/14
See application file for complete search history.

(56) References Cited

U.S. PATENT DOCUMENTS 4,220,561 A 9/1980 Winter et al. ............. 252/522 R

FOREIGN PATENT DOCUMENTS

EP 1 229 032 B1 8/2002

OTHER PUBLICATIONS

International Search Report PCT/IB2007/052263 Dated Jun. 20, 2008.

*Primary Examiner* — Taofiq A Solola
(74) *Attorney, Agent, or Firm* — Winston & Strawn LLP

(57) ABSTRACT

The present invention relates to 2-(3-methylbutyl)-4-propyl-1,3-oxathiane and its use as perfuming ingredients. The present invention also concerns the use of this compound in the perfumery industry as well as the compositions or articles containing this compound.

7 Claims, No Drawings

OXATHIANE DERIVATIVE AS PERFUMING INGREDIENT

This application is a 371 filing of International Patent Application PCT/IB2007/052263 filed Jun. 14, 2007.

TECHNICAL FIELD

The present invention relates to the field of perfumery. More particularly, it concerns 2-(3-methylbutyl)-4-propyl-1,3-oxathiane which is a useful perfuming ingredient. The present invention concerns also the use of said compounds in the perfumery industry as well as the compositions or articles containing said compound.

PRIOR ART

To the best of our knowledge, the invention's compound is new.

The closest prior art is represented by the compound 2-pentyl-4-propyl-1,3-oxathiane, described in U.S. Pat. No. 4,220,561, i.e. a structural isomer of the invention's compound. However, this prior art compound possesses an odor totally different from the one of the present invention and thus does not suggest the organoleptic properties of the compounds of formula (I), or any use of said compound in the field of perfumery.

DESCRIPTION OF THE INVENTION

We have now surprisingly discovered that a compound of formula

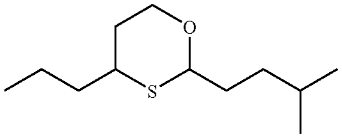

(I)

in the form of any one of its stereoisomers or a mixture thereof; can be used as perfuming ingredient, for instance to impart odor notes of the sulfury, cassis type.

In particular, the odor of 2-(3-methylbutyl)-4-propyl-1,3-oxathiane has fruity, herbaceous type notes. The fruity note is the one giving to the invention's compound its character, and said note is of the cassis, grapefruit type and is characterized by a very clean sulfury connotation, not having an alliaceous/onion/transpiration connotation as other ingredients of similar structure.

When the organoleptic properties of the invention's compound are compared with the ones of prior art compound of 2-methyl-4-propyl-1,3-oxathiane (U.S. Pat. No. 4,220,561), then the odor of compound (I) distinguishes by lacking an alliaceous/transpiration connotation, which is characteristic of the prior art compound.

When the organoleptic properties of the invention's compound are compared with the ones of prior art compound of 2-pentyl-4-propyl-1,3-oxathiane (U.S. Pat. No. 4,220,561), then the odor of compound (I) distinguishes by lacking a violet leaves connotation, which is characteristic of the prior art compound.

In fact the odor of the invention's compound is surprisingly much closer to the one of 2-methyl-4-propyl-1,3-oxathiane rather than to the one of 2-pentyl-4-propyl-1,3-oxathiane, despite that structurally it is the opposite.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). In particular said method is to impart odor notes as above mentioned for the invention compound.

By "use of a compound of formula (I)" it has to be understood here also the use of any composition containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:

i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:

i) as perfuming ingredient, at least one compound of formula (I), as defined above, or an invention's perfuming composition; and
ii) a consumer product base;

is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 3% by weight, or even more, of the compounds of the invention based on the weight of the composition into which they are incorporated. Preferably concentrations of the order of 0.12% to 2.5%, or even 0.15% to 2.5%, are used. The invention compound can thus be used in relatively high concentration, which is an advantage since of simpler use.

Concentrations lower than these, such as in the order of 0.01% to 1% by weight, can be used when these compounds are incorporated into perfumed articles, percentage being relative to the weight of the article.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz.

Example 1

Synthesis of Compounds of Formula (I) by Using the Aldol Derivative of α-Damascone as Starting Material To a solution of 3-mercapto-1-hexanol (10.0 g) and Amberlyst® 15 (5.0 g) in dichloromethane (90 ml), was added over 10 minutes 4-methylpentanal (7.6 g) (obtained according to J. Woon Yang et al., Angew. Chem. Int. Edition, 43, 2004, 6660-6662), followed by 4 A molecular sieves (2 g). The reaction mixture was stirred at room temperature until no more conversion is observed (GC).

Then, the solids were filtered out. The solvents were distilled off and the desired 2-(3-methylbutyl)-4-propyl-1,3-oxathiane was obtained, after vacuum distillation with a short Vigreux column, in 87% yield (14.0 g, cis/trans=80/20):

$^{1}$H-NMR (major isomer): 0.87-0.98 (m, 9H, overlap with the trans isomer), 1.2-2.3 (m, 11H, overlap with the trans isomer), 3.02 (m, 1H), 3.53 (m, 1H), 4.18 (m, 1H), 4.67 (t, J=6 Hz, 1H)

$^{13}$C-NMR (major isomer): 13.9 (q), 19.3 (t), 22.5 (q), 27.9 (d), 33.7 (t), 34.1 (t), 34.5 (t), 38.5 (t), 42.2 (d), 70.0 (t), 83.8 (d)

Example 2

Preparation of a Perfuming Composition

A perfuming composition of the cassis type was prepared by admixing the following ingredients:

| Ingredient | Parts by weight |
|---|---|
| Citronellol | 60 |
| Corps Praline | 10 |
| Dipropyleneglycol | 200 |
| 10%* Crystal moss | 50 |
| Hedione ®[1)] | 250 |
| 10%* Neobutenone ®[2)] | 25 |
| Octalynol | 25 |
| Rose oxide | 25 |
| Pinenes | 250 |
| (Z)-3-Hexen-1-ol | 5 |
| Rhubofix ®[3)] | 25 |
| 2,2,5-Trimethyl-5-pentyl-1-cyclopentanone | 25 |
| 2,4-Dimethyl-3-cyclohexene-1-carbaldehyde | 25 |
| | 975 |

*in dipropyleneglycol

[1)]Methyl dihydrojasmonate; origin: Firmenich SA, Geneva, Switzerland

[2)]1-(5,5-Dimethyl-1-cyclohexen-1-yl)-4-penten-1-one; origin: Firmenich SA, Geneva, Switzerland

[3)]3',4-Dimethyl-tricyclo[6.2.1.0(2,7)]undec-4-ene-9-spiro-2'-oxirane; origin: Firmenich SA, Geneva, Switzerland The addition of 25 parts by weight of 2-(3-methylbutyl)-4-propyl-1,3-oxathiane to the above-described composition exalted the fruity-cassis character of the latter, and increased the juicy aspect. The sulfury note imparted by the invention's compound was very clean and totally devoid of any alliaceous or "exotic fruit" connotation.

The addition of 25 parts by weight of a 50% (in ethyl citrate) 2-methyl-4-propyl-1,3-oxathiane to the above-described composition modified substantially the olfactive properties of the latter. The fruity note was reinforced but more in the direction "exotic fruit", rather than cassis, and the sulfury note was clearly alliaceous and unpleasant.

The addition of 25 parts by weight of 2-pentyl-4-propyl-1,3-oxathiane to the above-described composition imparted a totally different olfactive effect and imparted a fatty, green-cucumber note as well as a violet leaves character. The fragrance thus obtained lost the fruity-cassis character to become fatty and unpleasant.

The invention claimed is:

1. A compound of formula (I):

(I)

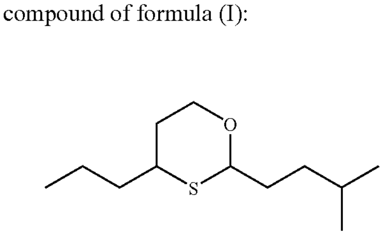

in the form of any one of its stereoisomers or a mixture thereof.

2. A method to confer, enhance, improve or modify the odor properties of a perfuming composition or of a perfumed article, which method comprises adding to said composition or article an effective amount of at least a compound of formula (I) according to claim 1.

3. The method according to claim 2, wherein the compound is added to a perfuming composition in an amount sufficient to impart a fruity note to the perfuming composition.

4. The method according to claim 2, wherein the compound is added to a perfumed article in an amount sufficient to impart a fruity note to the perfumed article.

5. A perfuming composition comprising:

i) as perfuming ingredient, a compound of formula (I)

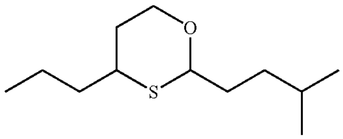

in the form of any one of its stereoisomers or a mixture thereof;

ii) at least one ingredient selected from the group consisting of a perfumery carrier and a perfumery base; and iii) optionally, at least one perfumery adjuvant.

6. A perfumed article comprising:

i) as perfuming ingredient, a compound of formula (I)

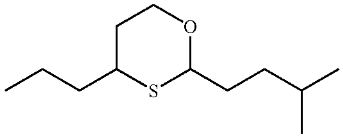

in the form of any one of its stereoisomers or a mixture thereof; and ii) a consumer product base.

7. The perfumed article according to claim 6, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

* * * * *